United States Patent
Nishiwaki et al.

(10) Patent No.: US 7,598,502 B2
(45) Date of Patent: Oct. 6, 2009

(54) CONFOCAL LASER SCANNING MICROSCOPE

(75) Inventors: Daisuke Nishiwaki, Hino (JP); Ikutoshi Fukushima, Fuchu (JP); Naobumi Okada, Asaka (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 11/964,483

(22) Filed: Dec. 26, 2007

(65) Prior Publication Data
US 2008/0156999 A1    Jul. 3, 2008

(30) Foreign Application Priority Data
Dec. 27, 2006   (JP) ............... 2006-353229

(51) Int. Cl.
*G01N 21/64* (2006.01)
(52) U.S. Cl. ................................... 250/458.1
(58) Field of Classification Search ........ None
See application file for complete search history.

(56) References Cited

U.S. PATENT DOCUMENTS

| | | | |
|---|---|---|---|
| 5,159,485 A | 10/1992 | Nelson | |
| 6,094,300 A * | 7/2000 | Kashima et al. | 359/385 |
| 6,399,935 B1 | 6/2002 | Jovin et al. | |
| 2003/0021016 A1* | 1/2003 | Grier | 359/368 |
| 2004/0113059 A1* | 6/2004 | Kawano et al. | 250/234 |
| 2006/0140462 A1 | 6/2006 | Saggau et al. | |
| 2006/0214106 A1 | 9/2006 | Wolleschensky et al. | |

FOREIGN PATENT DOCUMENTS

| | | |
|---|---|---|
| JP | H-10-206742 | 8/1998 |
| JP | 2006106336 A * | 4/2006 |

* cited by examiner

*Primary Examiner*—Constantine Hannaher
(74) *Attorney, Agent, or Firm*—Arnold International; Bruce Y. Arnold

(57) ABSTRACT

In a confocal laser scanning microscope that is equipped with a first scanning optical system for emitting an observation beam to scan and observe a sample and a second scanning optical system for emitting an excitation beam to scan and stimulate optically a part of the sample, the improvement of providing a micromirror device that simultaneously reflects the observation beam and the excitation beam as multiple sub-beams onto the sample. An optical scanning method using a confocal laser scanning microscope is disclosed that scans a sample with an observation beam and an excitation beam simultaneously using multiple observation beam spots and multiple excitation beams spots, thereby enabling events of short duration to be observed and/or recorded.

14 Claims, 9 Drawing Sheets

US 7,598,502 B2

CONFOCAL LASER SCANNING MICROSCOPE

This application claims the benefit of foreign priority under 35 U.S.C. §119 of JP 2006-353229 filed Dec. 27, 2006, the disclosure of which is hereby incorporated by reference.

BACKGROUND OF THE INVENTION

An experimental method is generally known wherein a desired location of a sample is irradiated with a laser beam (referred to herein as the 'excitation beam') for excitation of the sample while observing/recording reflected observation light and fluorescence from the sample so that changes in the appearance of the sample may be observed and/or recorded.

A laser scanning microscope for this purpose is disclosed in Japanese Laid-Open Patent Application H10-206742, which also discloses a scanning method. According to this scanning method, the entire sample may be scanned with an observation beam emitted by a first laser light source using a first scanning optical system while an arbitrary location of the sample is irradiated with an excitation beam emitted by a second laser light source using a second scanning optical system, and fluorescence from the sample may be detected with a photoelectric conversion element. In addition, other scanning methods may be used with a confocal laser scanning microscope, such as a method to deflect light utilizing a photo acoustic element, a method to deflect light using a galvanometer mirror, a method to direct light by rotating a pinhole disk called a Nipkow disc, and so on.

An example of the construction of a conventional laser scanning microscope that uses two pairs of galvanometer mirrors for scanning will now be discussed. As shown in FIG. 6, in a laser scanning microscope 10, a first scanning optical system 1 for observation includes an observation beam source 11 that emits an observation beam 22, a collimator lens 12, and a pair of galvanometer mirrors 14a, 14a' that perform (in the x-axis and y-axis directions) a two-dimensional scan of the observation beam 22. On the other hand, a second scanning optical system for excitation 2 includes an excitation beam source 19 that emits an excitation beam 23, a collimator lens 12, and a pair of galvanometer mirrors 14b, 14b' that perform, in the x-direction and y-direction, a two-dimensional scan of the excitation beam. In addition, a dichroic mirror 13a is positioned at a location where the observation beam 22 and the excitation beam 23 intersect one another. The dichroic mirror 13a transmits the observation beam 22 and reflects the excitation beam 23 so as to combine the two beams on a common optical path. A relay lens 15, an image-forming lens 16, and an objective lens 17 are placed along the common optical path, and a sample 18 is placed at the focal point of the objective lens 17. Also a dichroic mirror 13b is placed between the collimator lens 12 and the galvanometer mirror 14a in the light path of the first scanning optical system 1 so as to direct light reflected/emitted from the sample 18 (i.e., after the sample has been irradiated with the observation beam 22 and the excitation beam 23) to a detection optical system 3. The detection optical system 3 is formed of an image-forming lens 16, a pinhole 20, and a photoelectric conversion element 21. The pinhole 20 is used to block light rays other than those rays reflected/emitted at a conjugate point on the sample which is illuminated by the observation beam, since the pinhole 20 is positioned along the optical axis of light from the sample that has been reflected by the dichroic mirror 13b, and the pinhole 20 is positioned at the focal plane of the image-forming lens 16. In this way, optical information from the sample 18 can be measured with the photoelectric conversion element 21 which, for example, may be a photo multiplier.

Because the pair of galvanometer mirrors 14a, 14a' for the observation beam 22 and the pair of galvanometer mirrors 14b, 14b' for the excitation beam 23 are located and controlled independently, scanning of the observation beam and the excitation beam may be executed simultaneously and independently. For example, FIG. 7 shows a conventional sample scanning method using the observation beam 22 and the excitation beam 23, wherein the two galvanometer mirrors 14a, 14a' (see FIG. 6) of the first scanning optical system 1 are operated so as to scan the sample in two dimensions using the observation beam 22, and further, the two galvanometer mirrors 14b, 14b' of the second scanning optical system for excitation 2 are simultaneously operated in order to scan the sample in two dimensions using the excitation beam 23.

BRIEF SUMMARY OF THE INVENTION

The present invention relates to a confocal laser scanning microscope that is equipped with a micromirror device that enables one or two scanning beams to be divided into multiple subdivided beams (hereinafter termed sub-beams) that may be scanned simultaneously (e.g., as parallel sub-beams) so as to reduce the scanning time and thus increase the scanning rate. The micromirror device may also be controlled to scan the sub-beams in one direction of a two-dimensional scan, as well as to function as a pinhole.

BRIEF DESCRIPTION OF THE DRAWINGS

The present invention will become more fully understood from the detailed description given below and the accompanying drawings, which are given by way of illustration only and thus are not limitative of the present invention, wherein.

DETAILED DESCRIPTION

Figure 7:
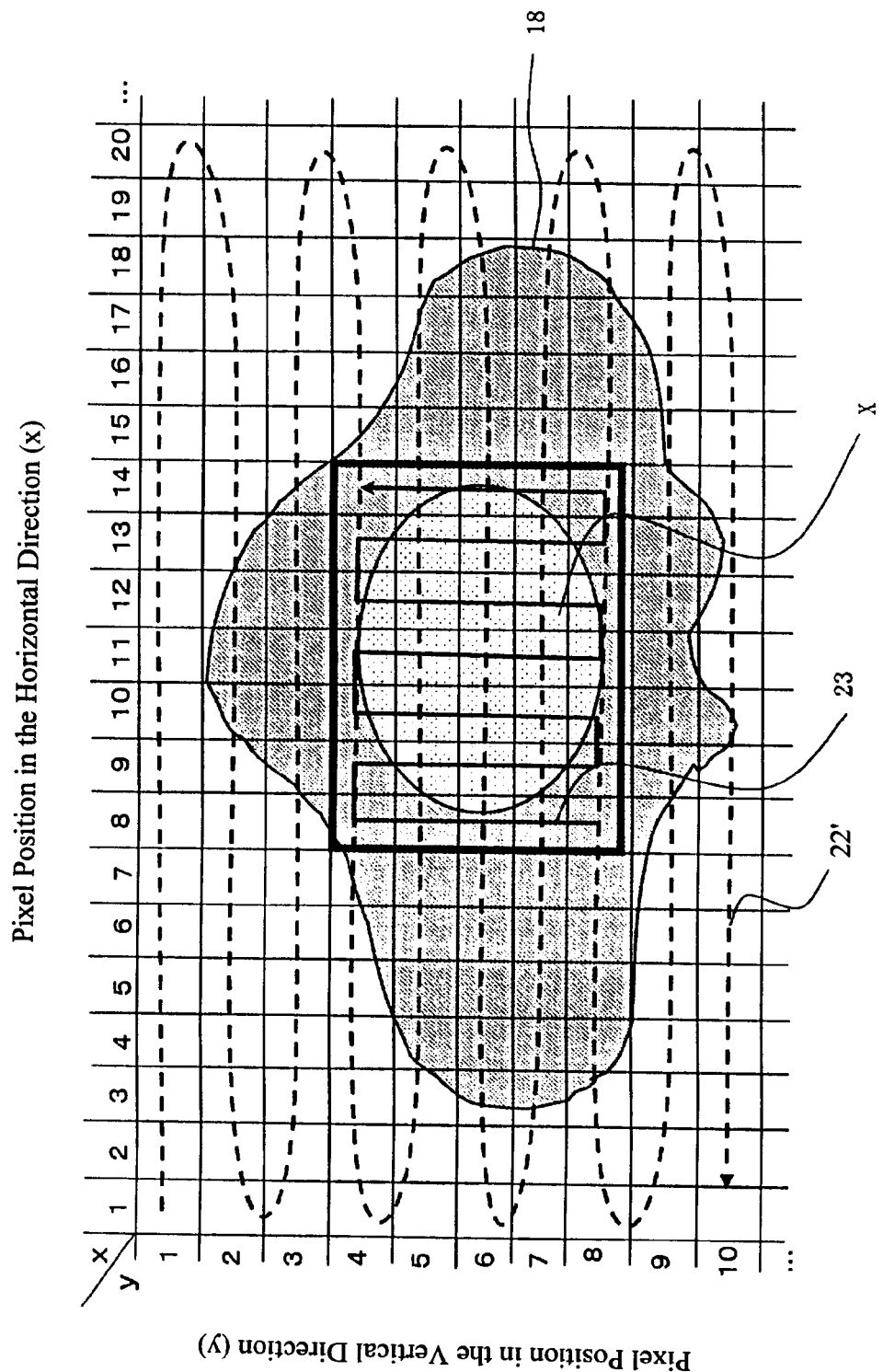
FIG. 7 is a chart showing a scanning method of the observation beam and the excitation beam in a conventional confocal laser scanning microscope.

Referring to prior art FIG. 7, which illustrates scanning a sample 18 using two galvanometer mirrors, the horizontal-axis direction in the figure will be regarded as the x coordinate and the vertical-axis direction will be regarded as the y coordinate, so that a position scanned with a beam may be expressed in terms of pixel coordinates (x, y). As can be seen by the dotted line, the scanning proceeds from the pixel (1, 1) to the pixel (2, 1) ... to the pixel (20, 1) so as to complete the first row of scanning. Then, scanning of the second row of pixels is performed in the reverse direction, and so on.

It will be assumed in the following explanation that a section X of a sample 18 is to be examined with an excitation beam 23. In other words, the fluorescent response of the section X is to be examined by illuminating this section with the excitation beam 23.

In the sample 18 according to the prior art example shown in FIG. 7, when an entire sample is to be scanned by irradiating the sample 18 with the observation beam 22, first, one galvanometer mirror (such as mirror 14a, shown in FIG. 6) of the first scanning optical system is rotated so as to scan the beam horizontally from the pixel position (1, 1) to the pixel position (20, 1). Next, the other galvanometer mirror (such as the mirror 14a', shown in FIG. 6) of the first scanning optical system 1 is rotated to move the observation position vertically to the pixel position (20, 2). Then, the other galvanometer mirror (i.e., mirror 14a) is rotated in the reverse direction from the direction it previously was rotated so as to scan the observation beam horizontally from the position (20, 2) to the position (1, 2). Next, galvanometer mirror 14a' of the first scanning optical system 1 is rotated to move to the beam vertically to the position (1, 3). This procedure then continues to the position (1, 10) as shown by the observation scan passage line 22' in FIG. 7, at which point it begins again at the position (1, 1), and so on.

In the same manner, with the excitation beam 23 of the second scanning optical system, the galvanometer mirror 14b may be used to scan horizontally and the galvanometer mirror 14b' may be used to scan vertically in the same manner as in the first scanning optical system for the observation beam. However, when a sample section X to be irradiated with the excitation beam 23 is within a rectangular area defined by the pixel positions (8, 4), (14, 4), (14, 8), and (8, 8) as shown in FIG. 7, only the area X is scanned with the excitation beam (in a manner similar to scanning with the observation scan passage line 22').

By simultaneously performing scans with the observation beam 22 and the excitation beam 23, fluorescence emitted from the sample takes a reverse course on the light path traveled by the observation beam 22 and the excitation beam 23 in irradiating the sample and passes through the dichroic mirror 13a and is reflected by the two galvanometer mirrors 14a', 14a of the first scanning optical system. Only the fluorescence wavelength from the sample is selectively reflected by the dichroic mirror 13b toward the light path of the detection optical system 3. Then, light from the sample reflected by the dichroic mirror 13b of the first scanning optical system is focused by the image-forming lens 16 of the detection optical system 3, passes through the pinhole 20, and reaches the photoelectric conversion element 21, wherein optical information of the sample is captured. Based on the optical information captured by the photoelectric conversion element 21, an image is created using an information processing device (not shown) and the fluorescent response of the sample to the excitation beam can be recorded.

As described above, a conventional scanning method using a confocal laser scanning microscope typically uses galvanometer mirrors to direct the scanning beams.

Figure 8A:
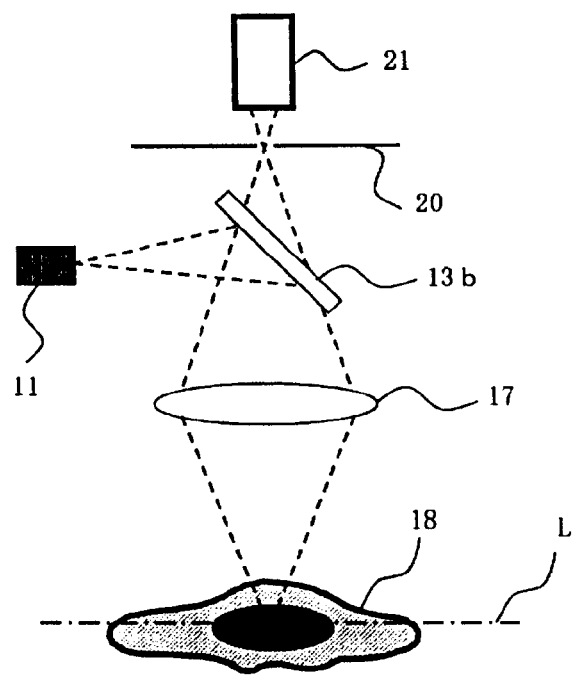
FIG. 8A shows the effect of a pinhole in that optical information at a depth L of a sample can be stored in a photoelectric conversion element when it is irradiated with an observation beam.
Figure 8B:
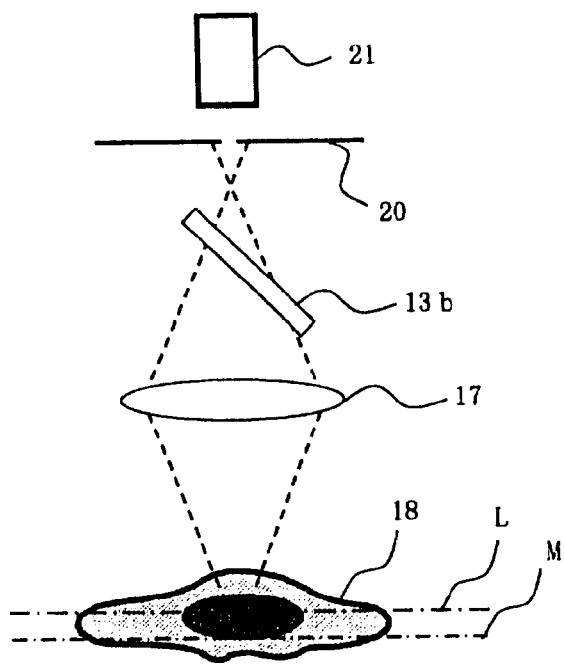
FIG. 8B shows that the majority of optical information at a depth M of the sample is not stored in the photoelectric conversion element due to the effect of a pinhole since optical information from other than the depth L of the sample is blocked by the pinhole and does not reach the photoelectric conversion element.

Referring to FIGS. 8A and 8B, the role of the pinhole 20 in the conventional confocal laser scanning microscope shown in FIG. 6 will now be explained. The pinhole 20 serves an important function in detecting three-dimensional information of the sample 18 (shown in FIG. 7), namely, information in the depth direction of the sample.

In FIGS. 8A and 8B, only an observation beam 11, a dichroic mirror 13b, an objective lens 17, the sample 18, a pinhole 20, and a photoelectric conversion element 21 are shown for simplicity of illustration of the operation of a conventional confocal laser scanning microscope. In FIG. 8A, it will be assumed that only optical information at a depth L of the sample 18 is to be obtained, and thus the pinhole 20 is adjusted so that the focal point of the objective lens corresponds to the depth L of the sample 18.

The passage of the observation beam until it is incident onto the photoelectric conversion element 21 shown in FIGS. 8A and 8B will now be described. First, the observation beam in FIGS. 8A and 8B is reflected by the dichroic mirror 13b, converted into a converging light flux by the objective lens 17, and focused at a depth L in FIG. 8A and at a depth M in FIG. 8B. Fluorescence emitted from a fluorescent material inside the sample at the depth L is collected by the objective lens 17, passes through the dichroic mirror 13b, and reaches the pinhole 20. Because the positions of the pinhole 20 and the focus point in FIG. 8A have been adjusted to be at optically conjugate positions of the objective lens 17, fluorescence emitted from the focal point will pass through the pinhole and be captured by the photoelectric conversion element 21. On the other hand, as shown in FIG. 8B, fluorescence emitted from the sample at a different depth M from the focal plane of the objective lens 17 that is collected by the objective lens 17 will be blocked by the pinhole 20 due to this light being in an unfocused state at the plane of the pinhole.

Thus, by using a pinhole in a confocal microscope, as described above, optical information at only the focal plane of the objective lens can be detected by a photoelectric conversion element in a confocal microscope. Therefore, information in the depth direction can be obtained by adjusting the position of the focal plane of the objective lens 17 relative to the sample, and by combining this information with optical information obtained by two-dimensional scanning of the observation beam, three-dimensional information of the sample 18 can be obtained.

Figure 6:
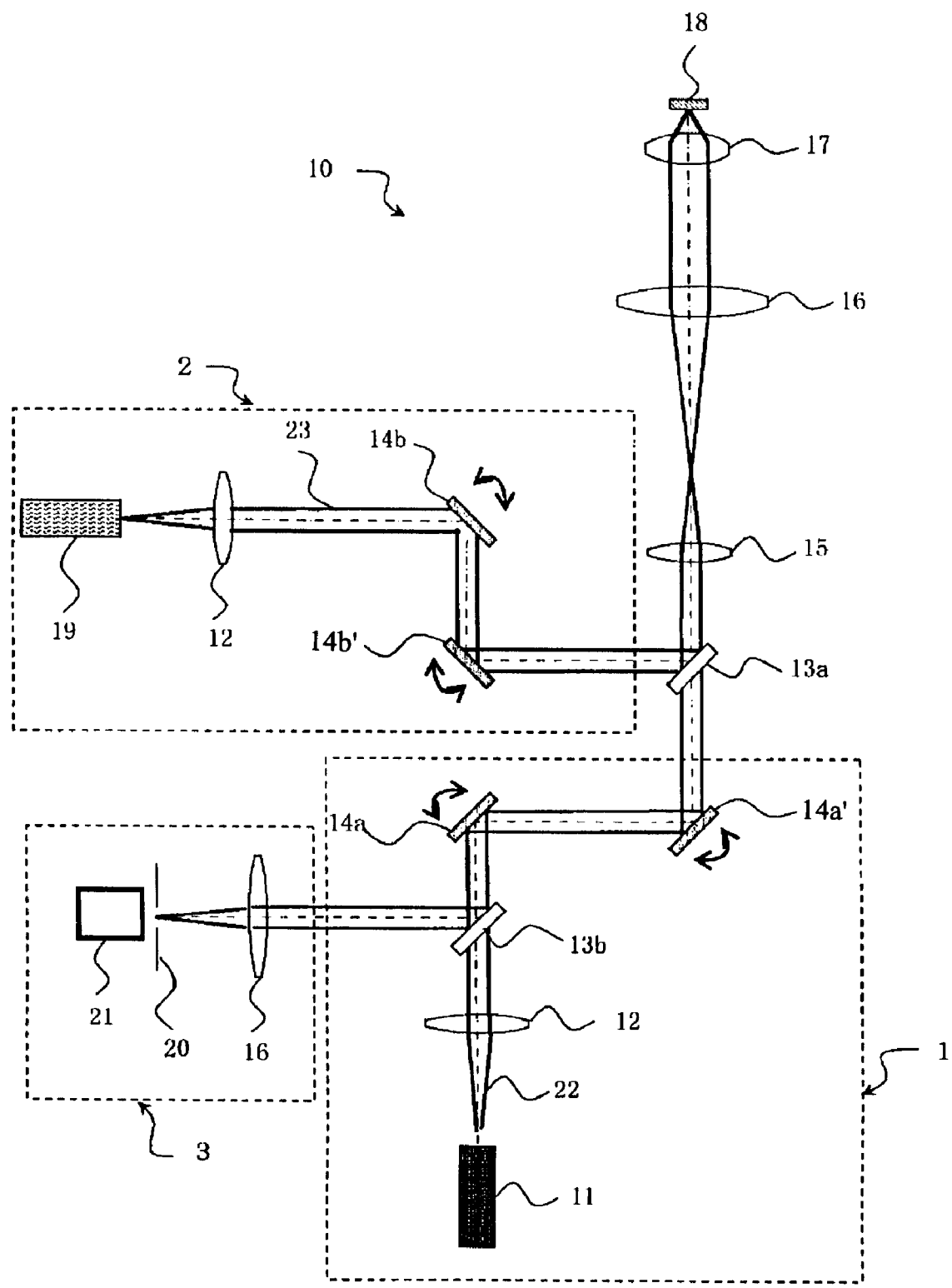
FIG. 6 shows the construction of a conventional confocal laser scanning microscope.

However, in a conventional confocal laser scanning microscope as shown in FIG. 6 and discussed above, there is a problem in that a relatively long time is required in order to scan with both the observation beam and the excitation beam so as to obtain an image of the fluorescence from the sample. Because of this, it is difficult to obtain an image at nearly a real-time rate, (i.e., at a motion picture rate) and this difficulty imposes a significant restriction in being able to adequately detect events of short duration as often occur in biological samples such as cells. In addition, in a confocal scanning microscope that uses a Nipkow disc (which can scan a sample at a motion picture rate), because the sample surface is scanned by condensing the observation beam onto multiple sections of the sample surface, the excitation beam cannot be irradiated onto only an arbitrary portion of the sample using a Nipkow disc. Therefore, a confocal laser scanning microscope is needed that can irradiate an excitation beam onto only an arbitrary portion of a sample while observing the sample at a motion picture rate.

In addition, digital micromirror devices (hereinafter referred to as DMDs) are generally known wherein a large number of micromirrors are arranged in a plane on a 'micro electro mechanical system device' (hereinafter referred to as a MEMS device) having electric circuits integrated on a single silicon substrate. In these DMDs, multiple micromirrors are arranged in rows and columns on a substrate, and a Coulomb force is generated by applying an electric voltage to two address electrodes that are positioned below each micromirror. The resulting Coulomb force causes the inclination angle of the micromirror above those address electrodes to toggle to a different inclination angle, and in this way the reflection of the incident light onto any particular micromirror may be controlled. Incident light that is reflected by a micromirror in the direction that irradiates the sample will be hereinafter termed an "ON beam". On the other hand, light reflected in other directions will be hereinafter termed an "OFF beam".

In conventional confocal laser scanning microscopes, because the whole or a specific area of a sample needs to be scanned with both of two laser beams, namely an excitation beam and an observation beam that are each condensed onto a section of the sample surface, there was a problem in that a relatively long time period was required to perform the scans with both the observation beam and the excitation beam so as to obtain an image of the fluorescence. Because of this, it was difficult to obtain fluorescent images at sufficiently high rates, such as the image rate used in motion pictures. This imposed a significant restriction in being able to view fluorescent responses of short duration, as often occur in samples such as biological cells.

In addition, in a conventional confocal laser scanning microscope, two galvanometer mirrors are required to perform a two-dimensional scan with a single light beam. In addition, a pinhole was required in order to obtain three-dimensional observation information from a sample.

The objective of the present invention is to provide, in a confocal laser scanning microscope, high-speed scanning of a sample that uses both an observation beam and an excitation beam.

As a first embodiment of a confocal laser scanning microscope according to the present invention, a confocal laser scanning microscope is equipped with a first scanning optical system for scanning with an excitation beam for stimulating fluorescent emissions, and a second scanning optical system for scanning with an observation beam so as to observe reflected light from the observation beam and the fluorescent response of the sample to the excitation beam. This embodiment is characterized by including a micromirror device that can reflect the observation beam and the excitation beam simultaneously to multiple points.

It is preferred that the excitation beam from the first scanning optical system be condensed onto the micromirror device using an anamorphic lens that corresponds to the first scanning optical system, that the observation beam from the second scanning optical system is condensed onto the micromirror device using an anamorphic lens that corresponds to the second scanning optical system, and that the light-condensation areas of the excitation beam and the observation beam form a line on the micromirror device.

In addition, it is preferred that the light-condensation areas of the excitation beam and the observation beam on the micromirror device coincide with a partial array of the mirror element array structure of the micromirror device.

Further, it is preferred that the micromirror device be placed at a position that is an optical conjugate position to the focal plane of the objective lens, and that scanning with the excitation beam and the observation beam be performed using a deflecting element that is placed at a position that is optically conjugate to the pupil position of the objective lens.

Moreover, it is desirable that the light-condensation areas of the excitation beam and the observation beam on the micromirror device intersect perpendicularly with the scanning direction of the deflecting element.

In addition, it is preferred to subdivide the observation beam and the excitation beam into multiple parallel sub-beams by reflecting these two beams, which are incident onto the micromirror device from two different directions, so that each sub-beam is directed in a common direction by a different micromirror of the micromirror device.

It is further preferred to place a dichroic mirror in the first scanning optical system and to place a line sensor at a position that is optically conjugate to the position of the micromirror device for detecting fluorescence.

In addition, it is preferred to place a dichroic mirror in the first scanning optical system, to place a deflecting element at a pupil position formed by a relay lens, and to scan in a direction that is perpendicular to the light-condensation area of the observation beam on the micromirror device for guiding light onto a two-dimensional detector.

Next will be discussed a scanning method using a confocal laser scanning microscope according to the present invention that simultaneously scans multiple parallel sub-beams as multiple observation beam spots and multiple excitation beam spots that are incident onto a sample surface.

In the confocal laser scanning microscope of the present invention, because the observation beam and the excitation beam may be subdivided using a micromirror device, the observation beam and the excitation beam can be simultaneously scanned as parallel sub-beams of observation beam light and excitation beam light. Thus, a sample can be scanned at a much higher speed than by using a conventional confocal laser scanning microscope. By using high-speed scanning as provided by the present invention, many more images can be obtained during a given period of time than previously. Thus, the present invention makes possible the detecting and viewing of events of short duration, as often occur in samples such as biological cells, that could not be detected and viewed using prior art techniques.

In addition, whereas previously, a pair of deflecting elements (such as galvanometer mirrors) were required to perform a two-dimensional scan with one beam, and two pairs of deflecting elements were required to scan in two dimensions with two beams, the present invention, by reason of the apparatus including a micromirror device, can perform a two-dimensional scan with two beams that are reflected from the micromirror device as parallel sub-beams using a single micromirror device and a pair of deflecting elements (such as a pair of galvanometer mirrors).

Furthermore, by the confocal laser scanning microscope of the present invention including a micromirror device, the micromirror device itself is capable of performing the role of a pinhole as used in a conventional confocal laser scanning microscope. Thus, the present invention makes unnecessary equipping the confocal laser scanning microscope with an actual pinhole.

The objective of the present invention is to enable high-speed scanning of a sample by a confocal laser scanning microscope that uses an observation beam and an excitation beam to scan the object, wherein there is provided in the confocal laser scanning microscope: a first scanning optical system for scanning with an observation beam to observe the sample; a second scanning optical system for scanning with an excitation beam for stimulating a part of the sample; and a micromirror device which can simultaneously reflect the observation beam and the excitation beam to multiple points.

Three embodiments of the present invention will now be described with reference to the drawings.

Embodiment 1

The construction and operation of Embodiment 1 of a confocal laser scanning microscope equipped with a micromirror device according to the present invention will now be described.

Figure 1A:
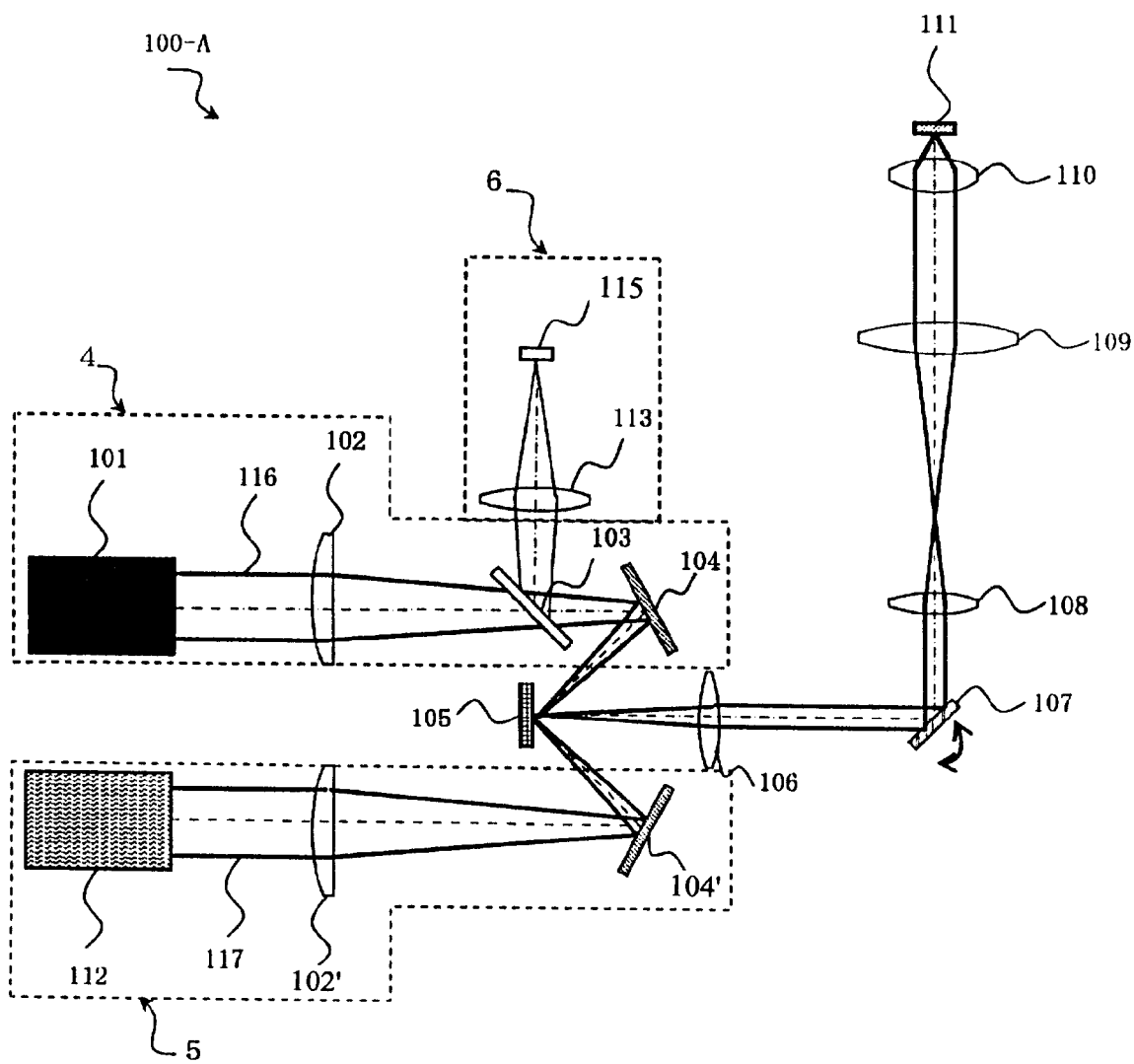
FIG. 1A shows the construction of a confocal laser scanning microscope that is equipped with a micromirror device according to a first embodiment of the present invention.

Referring to FIG. 1A, a confocal laser scanning microscope 100-A is shown that includes: a first scanning optical system 4 having an observation beam source 101 that emits an observation beam 116 that is then incident on an anamorphic lens 102 and a mirror 104; and a second scanning optical system 5 for excitation having an excitation beam source 112 that emits an excitation beam 117 that is then incident on an anamorphic lens 102' and a mirror 104'. A micromirror device 105 is placed at a location where reflected beams 116 and 117 from the mirrors 104, 104', respectively, intersect each other. If the micromirror device 105 is placed at the focal position of the two anamorphic lenses 102, 102' that are similar and are similarly oriented, the observation beam 116 and the excitation beam 117 may both be condensed onto mirror elements that form a single line on the micromirror device 105. It is preferred that the anamorphic lenses 102, 102' be similarly formed and similarly aligned so that the light-condensation directions of the observation beam 116 and the excitation beam 117 are aligned so as to be condensed onto the same line. Further, it may be arranged so that the light-condensation areas of the observation beam 116 and the excitation beam 117 coincide with a partial array of the mirror element array structure of the micromirror device 105. The anamorphic lenses in FIG. 1A are cylindrical lenses. A relay lens 106 and a relay lens 108 are positioned on a common light path following reflection of the observation beam 116 and the excitation beam 117 by the micromirror device 105. Between the relay lenses 106 and 108 is positioned a one-dimensionally-scanning galvanometer mirror 107 that serves as a deflecting element. Following the relay lens 108, an image-forming lens 109 and an objective lens 110 are placed in that order so as to image the two collinear beams onto a sample 111 that is placed at the focal plane of the objective lens 110. In this embodiment, the micromirror device 105 and the sample 111 are at optically conjugate positions of the lens system formed by the image-forming lens 109 and the objective lens 110. Further, it is preferred that the galvanometer mirror 107 is positioned so as to be optically conjugate to the pupil position of the lens system formed by the image-forming lens 109 and the objective lens 110. The observation beam 116 and the excitation beam 117, that are collinear after being reflected by the micromirror device 105, are then scanned by the galvanometer mirror 107.

The scan direction of the galvanometer mirror 107 is made to be approximately perpendicular to the direction of the line of micromirrors of the micromirror device onto which the observation beam 116 and the excitation beam 117 are condensed. Thus, the light-condensation areas of the observation beam 116 and the excitation beam 117 on the micromirror device intersect perpendicularly with the scan direction of the galvanometer mirror 107. Therefore, line scanning of the sample may be performed by merely scanning the single galvanometer mirror 107 in the directions indicated by the double-headed arrow adjacent the galvanometer mirror 107 in FIG. 1A.

A dichroic mirror 103 is positioned in the light path of the first scanning optical system 4 between the anamorphic lens 102 and the mirror 104 so as to direct fluorescence emitted by the sample 111 to a detection optical system 6 that detects the fluorescence emitted from the sample 111. The detection optical system 6 includes an image-forming optical system 113 that directs the fluorescence to a linear array of photoelectric conversion elements 115 that is placed at an optically conjugate position to the micromirror device and functions as a line sensor, so that fluorescence from the sample can be efficiently detected along a line. Further, optical information from the sample 111 that has been captured by the linear array of photoelectric conversion elements 115 may be reconstructed into an image by processing the information using an information processing device (not illustrated).

Embodiment 2

Figure 1B:
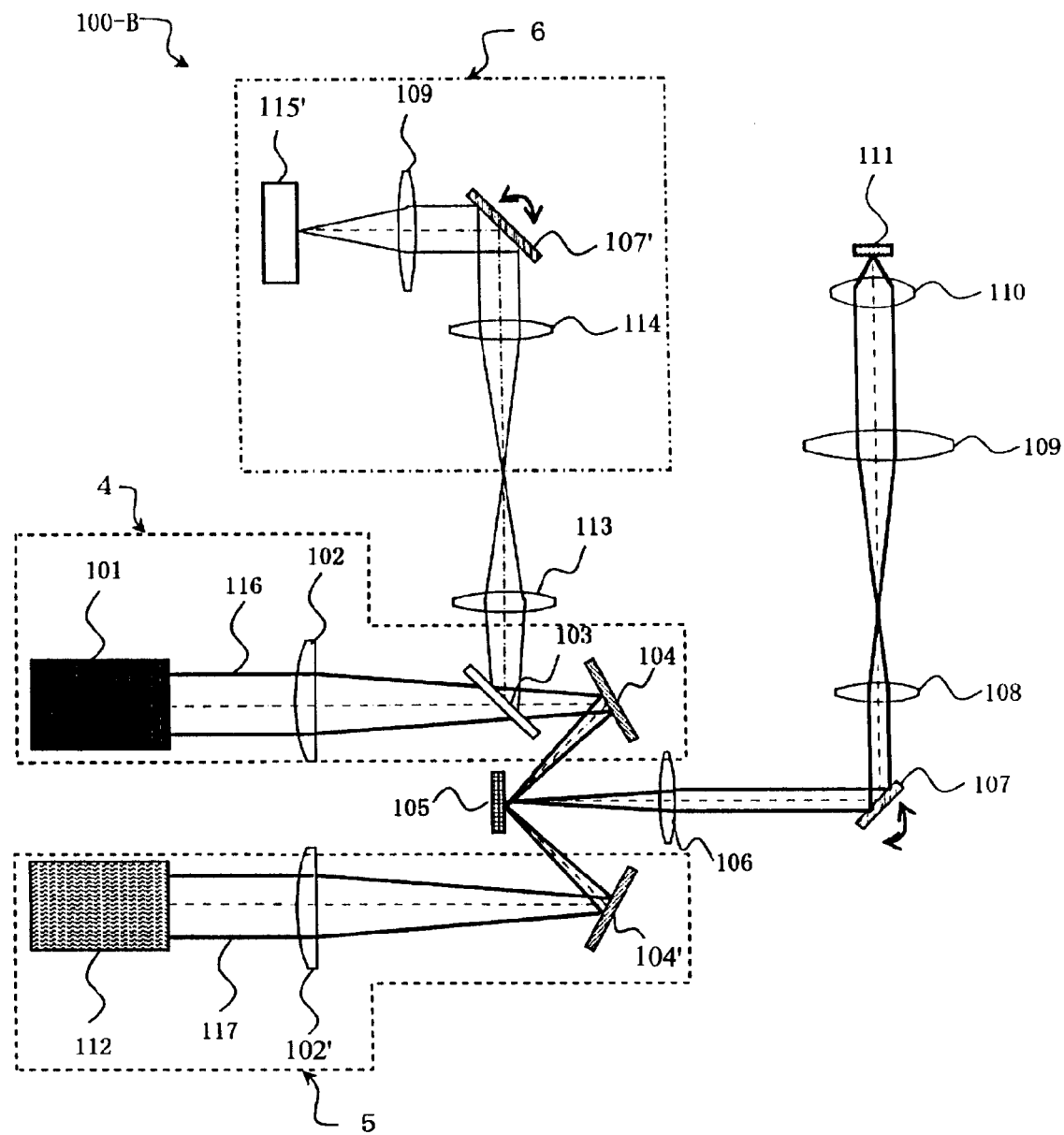
FIG. 1B shows the construction of a confocal laser scanning microscope that is equipped with a micromirror device according to a second embodiment of the present invention, wherein the detection optical system is different from that of the confocal laser scanning microscope in FIG. 1A.

FIG. 1B illustrates Embodiment 2 of a confocal laser scanning microscope 100-B that is equipped with a micromirror device according to the present invention. Except for a different construction of the detection optical system 6, the construction of this embodiment is very similar to that of Embodiment 1. Embodiment 2 differs from Embodiment 1 in that a two-dimensional array of detectors 115' is used instead of the linear array of photoelectric conversion elements 115 of FIG. 1A, and appropriate components are used in order to relay the linear light condensation pattern of the observation beam that is incident onto the micromirror device 105 to the two-dimensional array of detectors 115' and to scan this relayed image onto the two-dimensional array of detectors 115'. More specifically, a galvanometer mirror 107' is used to scan the light by rotating the galvanometer mirror back and forth (as shown by the double-headed arrow adjacent the galvanometer mirror 107') in synchronism with the rotation of the galvanometer mirror 107. As with the galvanometer mirror 107, the galvanometer mirror 107' is scanned in a direction perpendicular to the linear direction of the light condensation pattern of the observation beam on the micromirror device. An image-forming optical system 113 receives the fluorescence that has been reflected by the dichroic mirror 103 and condenses it to a pupil position. Collimating lens 114 is used to collimate the light that has passed through the pupil position, and the galvanometer mirror 107' is positioned in the light path following the collimating lens 114. The light from the dichroic mirror 103 that passes through the pupil position and the collimating lens 114 is then focused once again (after being scanned by the galvanometer mirror 107') onto the two-dimensional array of detectors 115', such as a CCD array, that captures the information. In this manner, two-dimensional fluorescent information of the sample 111 may be recorded.

Next, a method will be described for scanning an entire sample with an observation beam and an excitation beam using a micromirror device and a galvanometer mirror.

Figure 2:
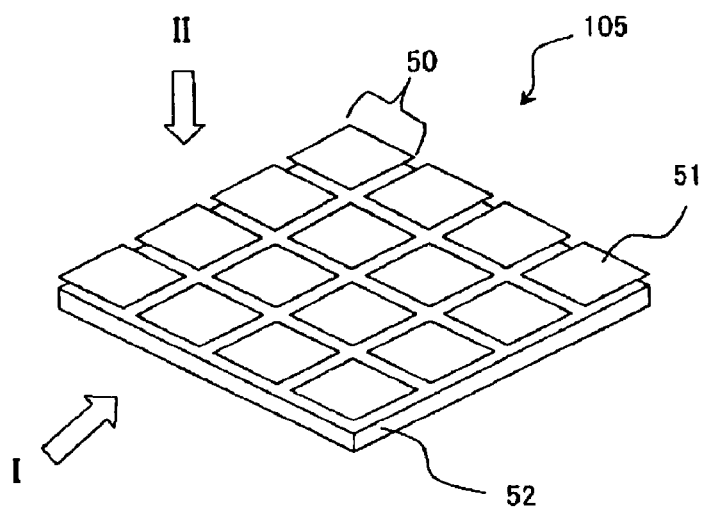
FIG. 2 illustrates mirror elements of the micromirror device arranged in two dimensions on a substrate.

FIG. 2 is an illustration of a micromirror device wherein mirror elements are arranged in two dimensions on a substrate. As shown in FIG. 2, the micromirror device 105 may have multiple mirror elements 50 arranged in rows and columns on a substrate 52. In this device, one micromirror 51 constituting one mirror element 50 is controlled with two electrodes (not illustrated) wherein the mirror plane of the micromirror 51 can be inclined as in FIG. 3 (that will be described later) by applying a voltage difference between the electrodes so that a Coulomb force is created. The Coulomb force is used to control the inclination of the plane of the micromirror 51 so as to control the direction of the light reflected by the micromirror 51. In this manner, the observation beam and the excitation beam can be controlled so as to be an ON beam or an OFF beam.

In the confocal laser scanning microscope of the present invention, the observation beam 116 from the first scanning optical system 4 and the excitation beam 117 from the second scanning optical system 5 are irradiated onto the micromirror device 105 from approximately symmetrically opposite directions relative to the normal of said micromirror device 105. Because the micromirror device 105 is placed at the focal point of the anamorphic lenses 102, 102', the observation beam and the excitation beam form a line image on the micromirror device 105. The light-condensation areas of the observation beam and the excitation beam in this line direction may be aligned with a particular direction of the mirror element array of the micromirror device 105. Thus, each of the mirror elements in the micromirror device may correspond to different pixels in scanning the sample in a particular direction, and the observation beam and the excitation beam may be condensed onto particular micromirrors of the micromirror device. In other words, pixels in a particular direction when scanning a sample can be controlled by controlling the micromirrors of the micromirror device, and the observation beam and the excitation beam may be condensed onto the micromirrors of the micromirror device in a line.

Figure 3:
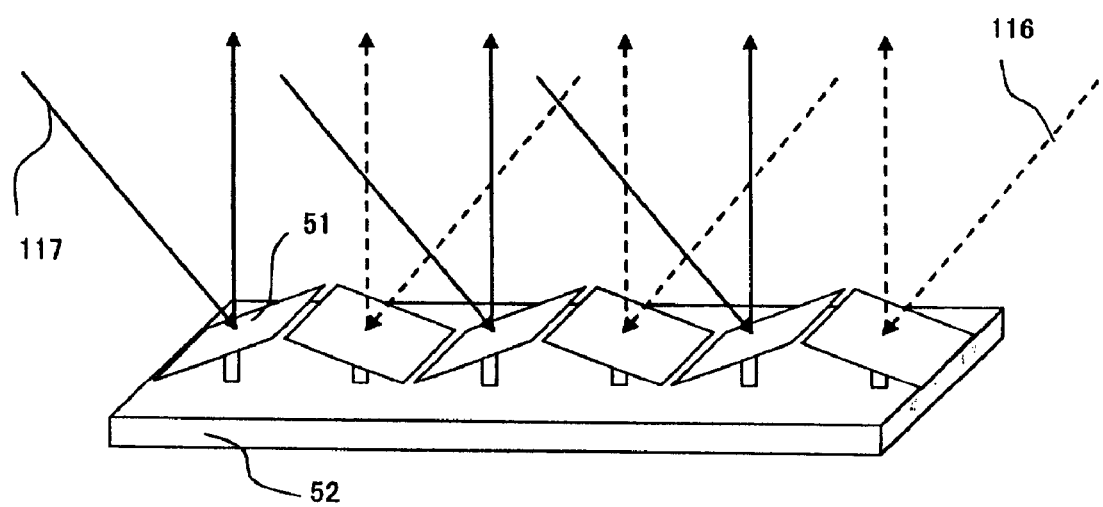
FIG. 3 illustrates an observation beam and an excitation beam that are incident from opposite directions (relative to the normal to a planar substrate surface of a micromirror device) being simultaneously divided and reflected as sub-beams toward a sample that is located in the direction of the normal to the planar substrate surface. This is accomplished by controlling the inclinations of adjacent micromirrors so that the micromirrors have inclinations that are equal and opposite relative to the direction of the normal to the planar substrate surface of the micromirror device.

FIG. 3 shows the substrate 52 and only a single row of the micromirrors 51, namely, the micromirrors nearest the arrow I shown in FIG. 2. The micromirrors 51 are shown in their ON orientations so that, when the micromirrors 51 are irradiated with the observation beam 116 and the excitation beam 117, the observation beam 116 and the excitation beam 117 are simultaneously reflected as ON beams (i.e., toward a sample), as will now be described. The micromirrors 51 are controlled so that the inclinations of adjacent micromirrors 51 become inclined in symmetrically opposite directions so that the observation beam 116 and the excitation beam 117 may be irradiated from symmetrically opposite directions relative to an axis that is normal to the plane of the micromirror device 105. In this manner, on a micromirror 51 that is inclined to the right in FIG. 3, the observation beam 116 will be reflected as an ON beam, and the excitation beam 117 will be reflected as an OFF beam (i.e., in a direction other than toward the sample). On the other hand, on a micromirror 51 that is inclined to the left in FIG. 3, the observation beam 116 will be reflected as an OFF beam, and the excitation beam 117 will be reflected as an ON beam. Moreover, the inclinations of the inclined micromirrors may be sequentially reversed (i.e., reversed in a time sequence), herein termed 'alternately reversed'. In addition, the micromirrors can also be oriented with their surfaces parallel with the plane of the substrate. This position has been termed the 'flat state' and is illustrated in FIG. 6 of US 2005/0286144 A1, the disclosure of which is hereby incorporated by reference. When in the flat state, each of the observation beam and the excitation beam will not be reflected toward to the sample; thus both beams are reflected as OFF beams when incident onto a micromirror in the flat state. In this manner, each of the observation beam 116 and the excitation beam 117 may be independently controlled so as to become an ON beam or an OFF beam by controlling the inclination direction of the mirror elements in the micromirror device. Therefore, by applying a voltage of a proper polarity (or by applying no voltage), to the electrodes of each mirror element constituting the micromirror device, the orientation of the micromirrors 51 to appropriate directions can be obtained, and switching of each mirror element can be independently controlled for each beam. Thus, the observation beam 116 can be made to be either an ON beam or an OFF beam after reflection from a given micromirror, and the excitation beam 117 can be made to be either an ON beam or an OFF beam after reflection from a given micromirror.

For example, the observation beam source 101 and the excitation beam source 112, can each be lasers for irradiating a sample. A micromirror device 105 (as illustrated in FIGS. 1A, 1B, and 3) reflects both beams as multiple sub-beams to a deflecting element (such as the galvanometer mirror 7) that then directs the light in a manner so as to scan the sample 111. As shown in FIG. 3, when every other mirror of the adjacent mirrors in a row or column of a micromirror device are in a first tilt position, they reflect light (illustrated by solid lines) from a first laser light source as multiple sub-beams that are not co-linear to the sample (as illustrated in FIGS. 1A and 1B). Light from a second laser source, when incident onto the same set of mirrors having the same tilt position, will be reflected as multiple sub-beams (not illustrated) in directions other than to the sample. On the other hand, light (illustrated by dashed lines in FIG. 3) from a second laser source, when incident onto a different set of micromirrors having an opposite tilt position, will be reflected as multiple sub-beams that are not co-linear to the sample. Moreover, light from the second laser source, when incident onto this same set of mirrors having the same tilt position, will be reflected as multiple sub-beams (not illustrated) in directions other than to the sample.

Next a scanning method will be described that scans the entirety of the sample 111 by simultaneously scanning multiple points with the observation beam 116 and the excitation beam 117 using a micromirror device and a galvanometer mirror.

Figure 4A:
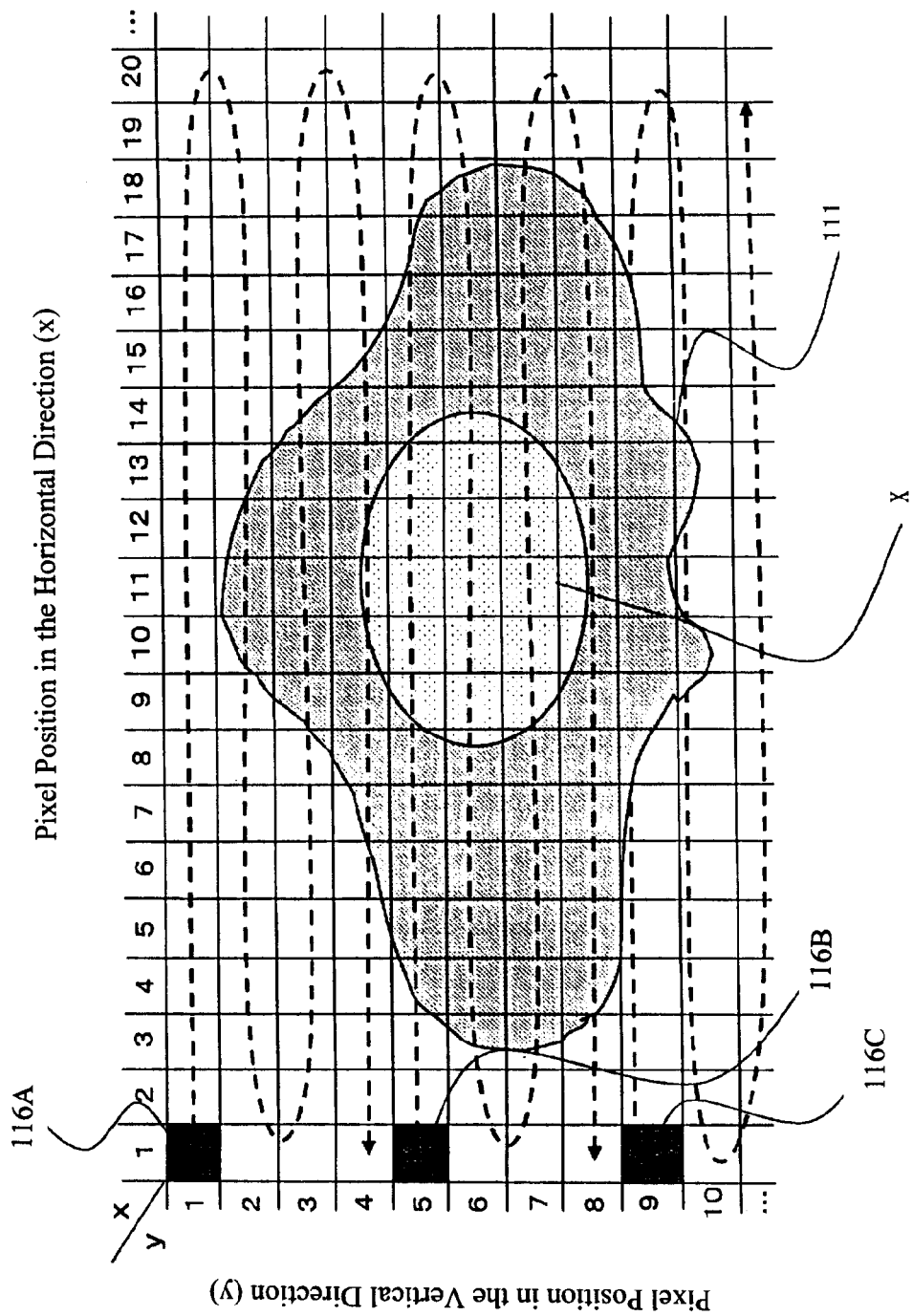
FIG. 4A illustrates a scanning method according to a first embodiment of the present invention, wherein an observation beam that is incident onto the mirrors of a micromirror device is divided into three sub-beams by selectively turning, at any given moment, three micromirrors in a linear array of micromirrors to the ON position, which is hereinafter defined as being the inclination that directs the beam reflected by a mirror toward a sample surface. The three sub-beams are then scanned in two dimensions by controlling which three micromirrors of the linear array are simultaneously turned to the ON position in conjunction with operating a galvanometer mirror. In other words, scanning in the horizontal direction x is performed by rotating a one-dimensionally-scanning galvanometer mirror, and scanning in the vertical direction y is performed by selecting which micromirrors of the linear array of micromirrors are simultaneously turned to the ON position.

FIG. 4A, for ease of illustration, shows scanning with only the observation sub-beams 116A, 116B and 116C. In other words, FIG. 4A illustrates the state wherein a scan area of the sample 111 is scanned with the observation beam 116 having been formed into three sub-beams that are parallel, with these sub-beams initially being directed at the pixel positions (1, 1), (1, 5) and (1, 9), with the scan progressing as indicated by three dashed lines that start in the horizontal direction from these positions. In the present invention, the galvanometer mirror 107 is used to scan the beams in the horizontal direction (i.e., along the rows labeled x in FIG. 4A). The micromirror device 105 has mirror elements arrayed linearly in a direction that corresponds to the vertical direction (i.e., along the columns labeled y in FIG. 4A). As will be described in more detail later, the scanning of pixels in the vertical direction can be accomplished by selecting which mirror elements of the micromirror device are selectively turned ON. Although the observation beam 116 could conceivably be condensed onto mirrors of a two-dimensional array of micromirrors and scanned by controlling each mirror element of the micromirror device to realize simultaneous, multiple-point scanning, it is preferred that the observation beam be condensed, at any one point in time, onto selected pixels that are arrayed in a given direction of the micromirror device 105. The reason for this is to be able to simulate, using a micromirror device, the same effect as produced by a pinhole, as will be described in detail later.

FIG. 4A shows an example of scanning with the observation beam according to the present invention by having the micromirror device simultaneously reflect three sub-beams (of observation beam light incident onto the micromirror device) towards the sample. This is accomplished by turning the micromirrors corresponding to pixels (1, 1), (1, 5) and (1, 9) to the ON position and leaving the remaining pixels in the row in the OFF position. Two galvanometer mirrors could be used to simultaneously scan these three pixels along the three scan lines shown by the three dashed lines. According to this example, by forming the observation beam into three sub-beams, the entire area of the sample can be scanned by making only two round-trip scans in the horizontal direction. (Note that, for convenience of illustration, only a part of the scan of the third beam, namely, the scan that originates with pixel (1, 9), is illustrated. Instead of using two galvanometer mirrors to simultaneously scan these three pixels along the three scan lines shown by the three dashed lines in FIG. 4A, the same scan can be achieved by using only a single galvanometer mirror. Once the galvanometer mirror has scanned the three beams to the far right of the rows Y=1, Y=5 and Y=9 (i.e., to pixel positions (20, 1), (20, 5) and (20, 9) for the return trip to the left, the mirror inclinations of the micromirrors corresponding to the pixels (1, 1), (1, 5) and (1, 9) can be switched to the Off position, and the micromirrors corresponding to the pixels (1, 2), (1, 6), and (1, 10) can be switched to the ON position, thus effectively changing the scan positions of the three sub-beams from the pixel positions (20, 1), (20, 5) and (20, 9) to the pixel positions (20, 2), (20, 6) and (20, 10). Then, once the single galvanometer mirror has scanned the three sub-beams back to the far left (i.e., to pixel positions (1, 2), (1, 6), and (1, 10), the micromirrors corresponding to the pixels (1, 2), (1, 6), and (1, 10) can be switched to the OFF position, and the micromirrors corresponding to the pixel positions (1, 3), (1, 7), and (1, 11) can be switched to the ON position, and so on. Therefore, by scanning a sample surface using galvanometer mirrors in order to deflect the scanning beam in a lateral direction, namely in a direction that is approximately perpendicular to a line of pixels that are arranged in a longitudinal direction on the micromirror device, multiple scanning beams that are arranged in parallel and condensed onto pixels in the longitudinal direction of the micromirror device can be simultaneously scanned, as shown in FIG. 4A. Therefore, the sample can be scanned at a higher speed than when the sample is scanned using a single scanning beam as in the prior art.

Embodiment 3

Figure 4B:
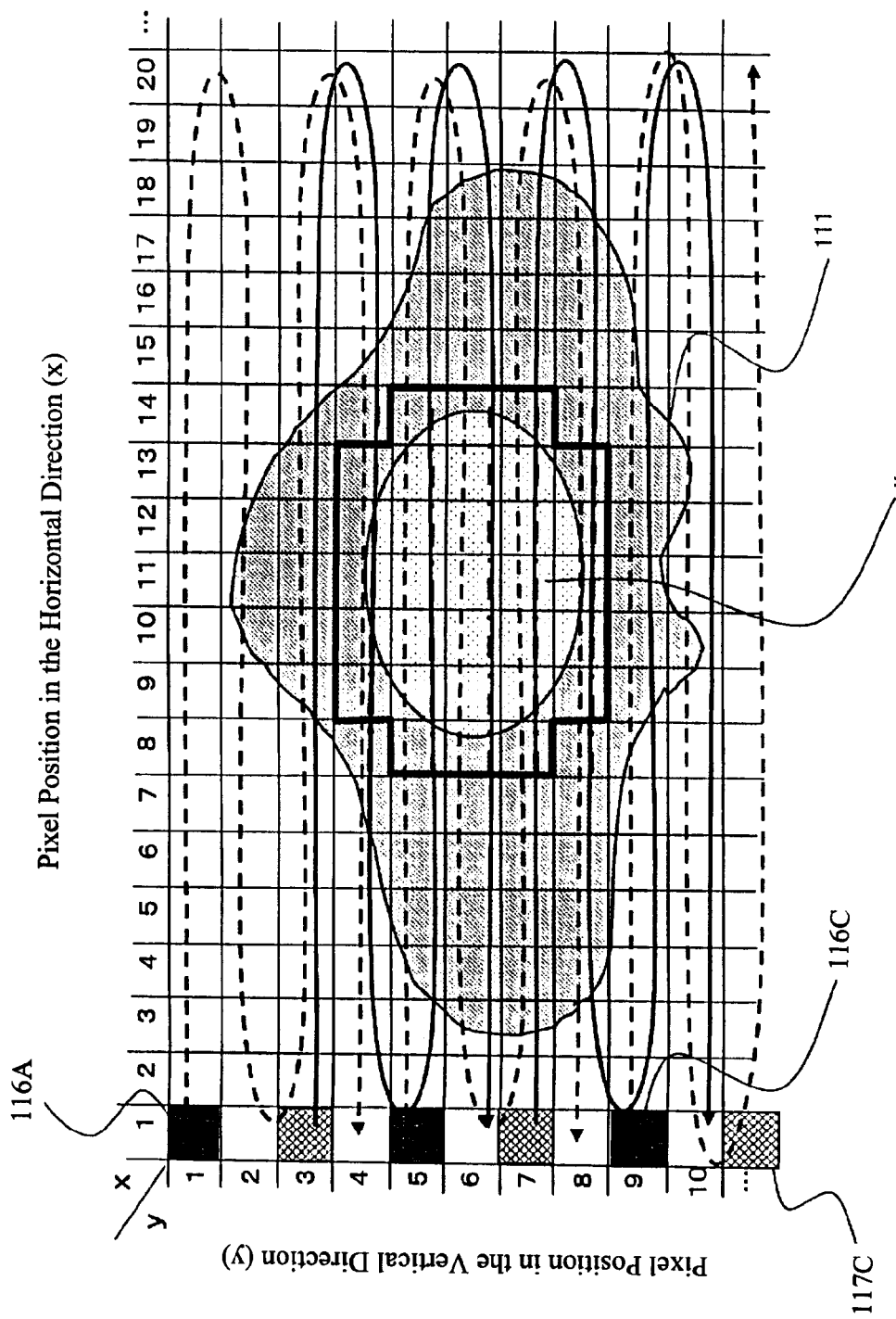
FIG. 4B illustrates a scanning method used in second and third embodiments of the present invention, wherein the observation beam and the excitation beam are positioned symmetrically opposed a normal to a substrate containing a linear array of mirror elements, and every other mirror element in a linear array at a given moment is turned to the ON position. Thus, both the observation sub-beam spots on the scanned surface (indicated by black pixels) and the excitation sub-beam spots on the scanned surface (indicated by cross-hatched pixels) may be scanned simultaneously using a single galvanometer mirror in conjunction with switching the ON/OFF positions of adjacent mirrors of the linear array of mirror elements.

In this embodiment, simultaneous multiple-point scanning with sub-beams formed from both the observation beam 116 and the excitation beam 117 may be performed. As shown in FIG. 4B, scanning is performed utilizing the observation sub-beams 116A, 116B, and 116C (shown in black) and the excitation sub-beams 117A, 117B, and 117C (shown in cross-hatch) that are reflected toward the sample by controlling the inclination of the micromirrors so that light is reflected to the shaded pixels, as shown in the left column of FIG. 4B. Notice that the excitation sub-beams 117A-117C are not always irradiated because only the oval-shaped area X shown in FIG. 4B may be of interest. The perimeter of the sample portion to be irradiated with light derived from the excitation beam 117 is indicated in the figure by a thick solid line.

In the scanning method shown in FIG. 4B, because the observation beam and the excitation beam are each divided into three sub-beams using the micromirror device, the scanning is completed by the deflecting element (i.e. the galvanometer mirror) making only two round-trip scans in the horizontal direction, just as in FIG. 4A. When switching to the return trip in a particular round trip, the inclinations of the mirror elements of the micromirror device are once again appropriately controlled, as discussed in detail with regard to FIG. 4A, so that the scan position is changed in the vertical direction without requiring a second galvanometer mirror to achieve a two-dimensional scan. Thus, the sample surface may be scanned in two dimensions using multiple parallel sub-beams of observation light and excitation light, and by using scanning galvanometer mirrors to deflect the beams only in the horizontal direction. By means of controlling the micromirrors that are selectively turned to the ON position, multiple pixels in the vertical direction may be simultaneously irradiated using multiple observation sub-beams, and multiple pixels in the vertical direction may be simultaneously irradiated using multiple excitation sub-beams.

As explained above, according to this embodiment of the present invention, because a sample can be observed while being irradiated simultaneously at multiple points with observation beams and excitation beams, optical information from the sample can be acquired faster than in the prior art. Therefore, the present invention makes it possible to detect information about events or reactions that have a short duration, such as those that occur in biological samples. The reason why the micromirrors that are turned to the ON state (i.e., the state for reflecting the observation beam 116 and the excitation beam 117 in the direction of the sample) are not closer together in this embodiment is so that a pinhole effect may be achieved in using the micromirror device. How close the micromirrors can be when in the ON state depends on the spot sizes of the observation beam and the excitation beam on the micromirror device and the size of the mirror elements of the micromirror device in the optical system.

Figure 5:
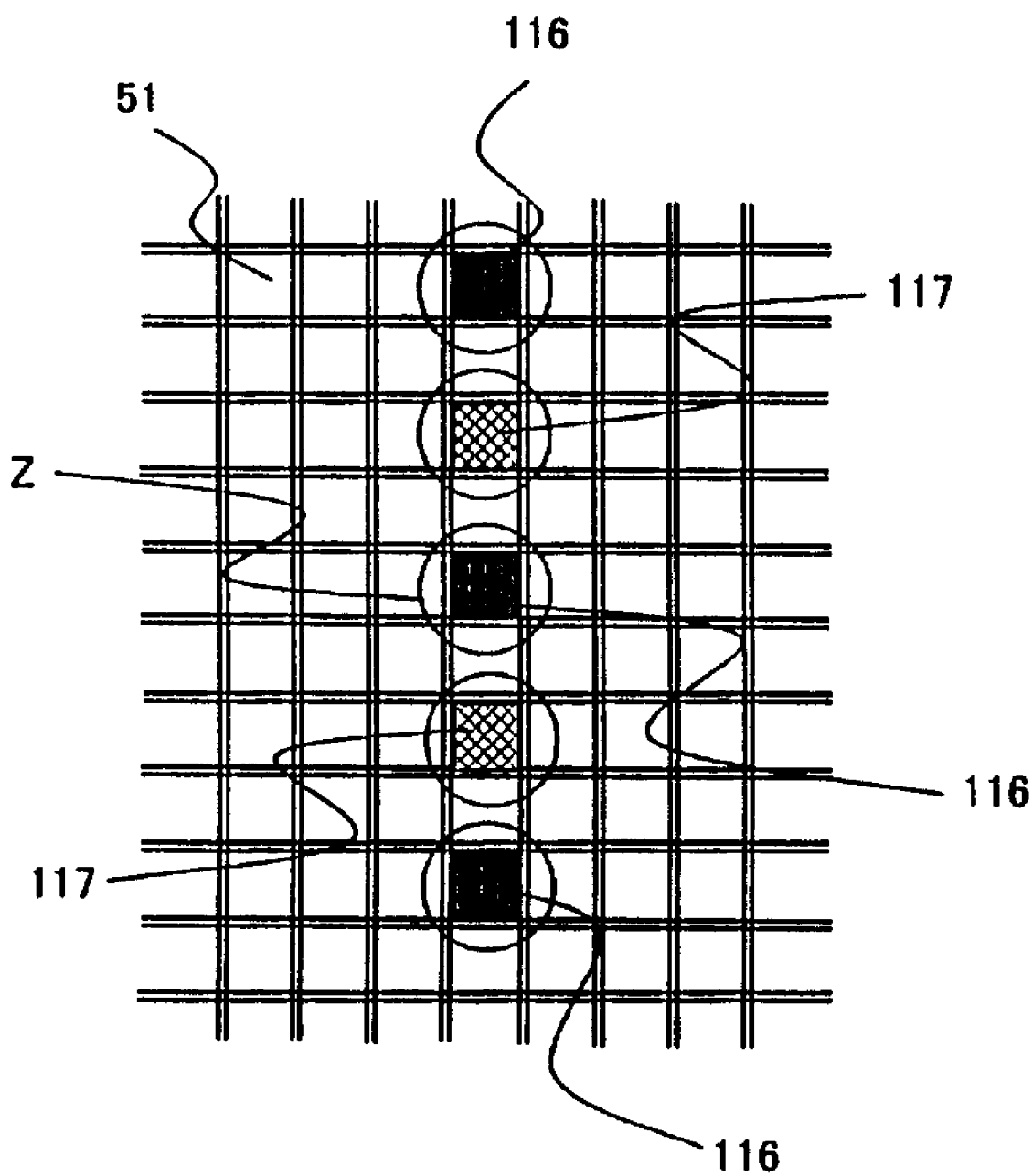
FIG. 5 shows the micromirror device in FIG. 2 as viewed in the direction of the line of sight (shown by the arrow II in FIG. 2), wherein the arrangement of the observation beam and the excitation beam on the micromirrors of the micromirror device can function as pinholes, as will be discussed later.

By providing a scanning microscope with a micromirror device, it is possible to divide the illumination beam and the excitation beam into multiple sub-beams that are directed as parallel beams that proceed in a common direction after being reflected by the micromirrors of the micromirror device (as shown in FIG. 3). The micromirror device, can also be used to perform the same function normally performed by a pinhole, as will now be explained with reference to FIG. 5, which illustrates the state of the micromirrors in FIG. 2 when viewed in the direction illustrated by the arrow II in FIG. 2. It is assumed in FIG. 5 that the observation beam 116 and the excitation beam 117 are reflected as ON beams by adjacent mirror elements of the micromirror device. The pixel within the circle labeled Z in FIG. 5 is the irradiation area of the observation beam 116. In order for a mirror element that reflects one of the incident observation beam and the incident excitation beam toward the sample when in the ON position to serve the function of a pinhole, reflection as an ON beam must occur with no overlap of spots. Thus, in order to bring about the same effect as in using a pinhole, adjacent micromirror elements that are to form different spots on the sample must not be set to the ON position. However, the mirror element to be regarded as a pinhole that forms a single spot need not necessarily be limited to a single micromirror element. For example, it would be possible to have a 2×2 grouping of four mirror elements in a two-dimensional array turned to the ON position simultaneously so as to correspond to a single spot so as to bring about a pinhole effect. Thus, several mirror elements of a micromirror device that are arranged side-by-side in two dimensions may be set to the ON position simultaneously in order to achieve a desired spot size.

While the present invention has been described using specific embodiments, it will be obvious that various modifications may be made to these embodiments without deviating from the spirit and scope of the invention. Therefore, the specification and drawings should not be construed as being limitative. Rather, the scope of the invention shall be defined as set forth in the following claims and their legal equivalents. All such modifications as would be obvious to one skilled in the art are intended to be included within the scope of the following claims.

What is claimed is:

1. A confocal laser scanning microscope that includes a first scanning optical system for the purpose of emitting an observation beam to scan and observe a sample, and a second scanning optical system for the purpose of emitting an excitation beam to scan and optically excite a part of said sample said confocal laser scanning microscope further comprising:
    an objective lens;
    a micromirror device, which includes a linear away of micromirrors, said observation beam and said excitation beam being incident from different directions, said micromirrors being controllable so as to form said observation beam and said excitation beam into a sub-beam pattern and to reflect the sub-beam pattern, said micromirrors located at a position that is conjugate to a focal plane of said objective lens;
    a first anamorphic lens in said first scanning optical system that condenses said observation beam from said first scanning optical system onto said micromirror device; and
    a second anamorphic lens in said second scanning optical system that condenses said excitation beam from said second scanning optical system onto said micromirror device;
    a one-dimensionally-scanning galvanometer mirror, that is positioned on the same side of said micromirror device as said sample and which reflects said observation beam that has been emitted from said first scanning optical system and reflected by said micromirror device and which reflects said excitation beam that has been emitted from said second scanning optical system and reflected by said micromirror device; wherein
    the combination of said micromirror device and said one-dimensionally-scanning galvanometer mirror simultaneously reflects each of said observation beam and said excitation beam to multiple points on said sample two-dimensionally.

2. The confocal laser scanning microscope according to claim 1, wherein said sub-beam pattern is incident onto one or more rows or one or more columns of micromirrors of said micromirror device.

3. The confocal laser scanning microscope according to claim 2, wherein
    the one-dimensionally-scanning galvanometer mirror is located at an optically conjugate position to the pupil position of said objective lens so as to scan the observation beam and the excitation beam.

4. The confocal laser scanning microscope according to claim 3, wherein the sub-beam pattern on said micromirror device is perpendicular to the direction said one-dimensionally-scanning galvanometer mirror scans the observation beam and the excitation beam.

5. The confocal laser scanning microscope according to claim 2, wherein adjacent mirror elements in a row or a column of said micromirror device are switched to opposite positions when scanning the observation beam and the excitation beam.

6. The confocal laser scanning microscope according to claim 1, wherein
    the one-dimensionally-scanning galvanometer mirror is located at an optically conjugate position to the pupil position of said objective lens so as to scan the observation beam and the excitation beam.

7. The confocal laser scanning microscope according to claim 6, wherein the sub-beam pattern on said micromirror device is perpendicular to the direction said one-dimensionally-scanning galvanometer mirror scans the observation beam and the excitation beam.

8. The confocal laser scanning microscope according to claim 1, wherein adjacent mirror elements in a row or a column of said micromirror device are switched to opposite positions when scanning the observation beam and the excitation beam.

9. The confocal laser scanning microscope according to claim 1, said confocal laser scanning microscope further including:
    a dichroic mirror in said first scanning optical system; and
    a line sensor located at a position that is optically conjugate to the position of said micromirror device.

10. The confocal laser scanning microscope according to claim 1, said confocal laser scanning microscope further including:
    a dichroic mirror in said first scanning optical system; and
    a relay lens; wherein
    the one-dimensionally-scanning galvanometer mirror is located at a pupil position of the relay lens and is movable in a direction that is perpendicular to the sub-beam pattern on said micromirror device so as to scan the sample.

11. The confocal laser scanning microscope according to claim 1, wherein:
    said micromirror device has a planar substrate that supports an array of adjacent micromirrors; and
    the adjacent micromirrors of said micromirror device are independently controllable so as to be inclined in symmetrically opposite directions in a row or a column so that the observation beam and the excitation beam may be irradiated from symmetrically opposite directions relative to an axis that is normal to the plane of said substrate, reflected by adjacent micromirrors of the micromirror device, and the inclinations of said micromirrors may be alternately reversed.

12. The confocal laser scanning microscope according to claim 11, wherein scanning in one direction is performed by rotating said one-dimensionally-scanning galvanometer mirror; and scanning in a direction perpendicular to said one direction is performed by selecting which micromirrors are sequentially controlled so as to reflect light to a sample via said one-dimensionally-scanning galvanometer mirror.

13. In an optical scanning method that scans a sample with an observation beam and an excitation beam using a confocal laser scanning microscope, the improvement of:

(a) using a micromirror device, which includes multiple micromirrors in a linear array, that are controlled so as to form multiple sub-beams that are not collinear of both the observation beam and the excitation beam; and (b) using a one-dimensionally-scanning deflecting element to scan the sample surface simultaneously using said multiple sub-beams.

14. A confocal laser scanning microscope that includes:

a first laser light source for irradiating a sample with an excitation beam;

a second laser light source for irradiating a sample with an observation beam;

a micromirror device, which includes a linear away of micromirrors, provided at a position conjugate to a focal plane of an objective lens, said micromirror device having a substrate that supports an array of adjacent micromirrors that may be tilted to opposite positions relative to a normal to said substrate; and a one-dimensionally-scanning deflecting element; wherein light is simultaneously directed from said first and second laser light sources so as to be incident onto the micromirror device;

the micromirrors of the micromirror device (a) when in one tilt position, reflect light from the first laser light source to the deflecting element as multiple sub-beams that are not collinear and do not reflect light from the second laser light source to the one-dimensionally-scanning deflecting element; and (b) when in another tilt position, reflect light from the second laser light source to the deflecting element as multiple sub-beams that are not collinear and do not reflect light from the first laser light source to the one-dimensionally-scanning deflecting element.

* * * * *